United States Patent [19]
Hutchinson et al.

[11] Patent Number: 4,990,626
[45] Date of Patent: Feb. 5, 1991

[54] PROCESS FOR PREPARING BISIMIDES PRODUCTS

[75] Inventors: Donald O. Hutchinson; Ali M. Dadgar; Keith G. Anderson, all of Baton Rouge, La.

[73] Assignee: Ethyl Corporation, Richmond, Va.

[21] Appl. No.: 332,984

[22] Filed: Apr. 4, 1989

[51] Int. Cl.$^5$ ............................................ C07D 209/48
[52] U.S. Cl. ................................................. 548/462
[58] Field of Search ........................................ 548/462

[56] References Cited

U.S. PATENT DOCUMENTS

| | | | |
|---|---|---|---|
| 3,868,388 | 2/1975 | Dotson et al. | 260/326 |
| 3,966,726 | 6/1976 | Toth et al. | 260/249.8 |
| 4,092,345 | 5/1978 | Wolford et al. | 260/501.16 |
| 4,125,535 | 11/1978 | Wolford | 548/462 |
| 4,374,220 | 2/1983 | Sonnenberg | 524/94 |
| 4,535,170 | 8/1985 | Sonnenberg | 548/462 |
| 4,581,396 | 4/1986 | Sonnenberg | 524/87 |

FOREIGN PATENT DOCUMENTS 0023420 of 0000 European Pat. Off. .
2926638 1/1981 Fed. Rep. of Germany .

Primary Examiner—Robert A. Wax
Assistant Examiner—F. Tsung
Attorney, Agent, or Firm—E. E. Spielman, Jr.; David E. LaRose

[57] ABSTRACT

In a first embodiment this invention relates to a process for preparing a white product which principally contains a bisimide. The process comprises: providing tetrabromophthalic anhydride and a solvent in a reaction vessel; forming, at a temperature within the range of from about 140° C. to about 200° C., a reaction mass by adding a diamine, a diamine salt or a mixture thereof to the solution, the formation of the reaction mass resulting in the production of a bisimide precipitate which becomes a component of the reaction mass; terminating the addition of the diamine when the molar ratio of the tetrabromophthalic anhydride initially present in the solution to the diamine or diamine salt added is substantially stoichiometric; cooking the bisimide precipitate to increase the average sphericity of the particles making up the bisimide precipitate; and recovering from the reaction mass, as the bisimide product, the cooked precipitate. In a second embodiment the cooking step is optional and the retention of water formed during the diamine or diamine salt addition is featured.

20 Claims, 1 Drawing Sheet

PROCESS FOR PREPARING BISIMIDES PRODUCTS

BACKGROUND OF THE INVENTION

This invention relates to an improved process for preparing a white halogenated bisimide product having good filterability.

As is taught in U.S. Pat. No. 4,374,220, there are a multitude of halogenated bisimides which are effective as flame retardants in formulation with macromolecular flammable materials, e.g. polymers. These formulations are useful in making articles such as wire insulation and electronic housings. Of the halogenated bisimides, the N,N'-alkylene-bis(tetrabromophthalimide)s are especially commercially significant.

A presently used commercial route for producing a product which principally contains N,N'-alkylene-bis(tetrabromophthalimide) comprises reacting tetrabromophthalic anhydride with a diaminoalkane in the presence of water and an alkanoic acid to yield a reaction mass containing the intermediate, N,N'-alkylene diammonium-bis(tetrabromophthalate). The reaction mass is then heated to about 225° C. for a period of about 2 hours to convert the intermediate to N,N'-alkylene-bis(tetrabromophthalimide) which is the principal constituent of the product recovered from the reaction mass. This product is particularly useful as it has good thermal stability and resistance to UV degradation. However, the product has a yellow color which argues against its presence in compositions used for forming white articles. Also, the intensity of the yellow color can vary between product batches, which color variance makes it difficult for the article manufacturer to maintain consistency in the color of the articles produced. The yellow color is believed to be due to impurities formed during the conversion of the N,N'-alkylene diammonium-bis(tetrabromophthalate) intermediate to the corresponding bisimide product.

U.S. Pat. No. 4,125,535 discloses a process for preparing a white product which is predominantly N,N'-alkylene-bis-(tetrabromophthalimide). The process features reacting tetrabromophthalic anhydride with diaminoalkane in an approximate 2 to 1 molar ratio. The reaction occurs in a solvent having a boiling point of least about 125° C. A preferred solvent is one comprised of about 70% by weight xylenes and about 30% by weight propionic acid. While this process produces a white product, it has been found that this product develops a yellow color or tint when subjected to the processing conditions used in producing articles from thermoplastic formulations.

It is, therefore, an object of this invention to provide a process for producing a white flame retardant product which principally contains N,N'-alkylene-bis(tetrabromophthalimide) or N,N'-bis(tetrabromophthalimide), which product does not experience significant color degradation and which product has good filterability.

THE INVENTION

A first embodiment of this invention relates to a process for preparing a white bisimide product which principally contains N,N'-alkylene-bis(tetrabromophthalimide) or N,N'-bis-(tetrabromophthalimide). The process features: providing, in a reaction vessel, a solution containing tetrabromophthalic anhydride and a solvent which contains at least about 15 wt % of a mono-, di- or tri- carboxylic acid having a dissociation constant not higher than $1.0 \times 10^{-3}$ at 25° C.; forming, at a temperature within the range of from 140° C. to about 200° C., a reaction mass by adding to the solution a diamine or a diamine salt formed by the partial or total diamine neutralization of a mono-, di- or tri- carboxylic acid having a dissociation constant not higher than $1.0 \times 10^{-3}$ at 25° C., such formation of the reaction mass resulting in the production of a bisimide precipitate which becomes a component of the reaction mass; terminating the addition of the diamine or diamine salt when the molar ratio of the tetrabromophthalic anhydride initially present in the solution to said diamine or diamine salt added is from about 1.9:1 to about 2.1:1; cooking, after the addition of the diamine or diamine salt, the bisimide precipitate at a temperature within the range of from about 140° C. to about 200° C. to obtain an increase in the average sphericity of the particles comprising such precipitate, the sphericity being defined as the ratio of the surface area of a sphere having the same volume of the particle being measured to the surface area of the particle; and recovering, as the bisimide product, the cooked bisimide precipitate.

A second embodiment of this invention relates to a process for preparing a white bisimide product which principally contains N,N'-alkylene-bis(tetrabromophthalimide) or N,N'-bis(tetrabromophthalimide). The process features: providing, in a reaction vessel, a solution containing tetrabromophthalic anhydride and a solvent which contains at least about 15 wt % of a mono-, di- or tri- carboxylic acid having a dissociation constant not higher than $1.0 \times 10^{-3}$ at 25° C.; forming, at a temperature within the range of from 140° C. to about 200° C., a reaction mass by adding to the solution a diamine or a diamine salt formed by the partial or total diamine neutralization of a mono-, di- or tri- carboxylic acid having a dissociation constant not higher than $1.0 \times 10^{-3}$ at 25° C., such formation of the reaction mass resulting in the production of a bisimide precipitate which becomes a component of the reaction mass; terminating the addition of the diamine or diamine salt when the molar ratio of the tetrabromophthalic anhydride initially present in the solution to said diamine or diamine salt added is from about 1.9:1 to about 2.1:1; retaining, during the formation of the reaction mass, a substantial portion of the water produced during such formation; and recovering, as the bisimide product, the produced bisimide precipitate.

DETAILED DESCRIPTION OF THE INVENTION

Figure 1:
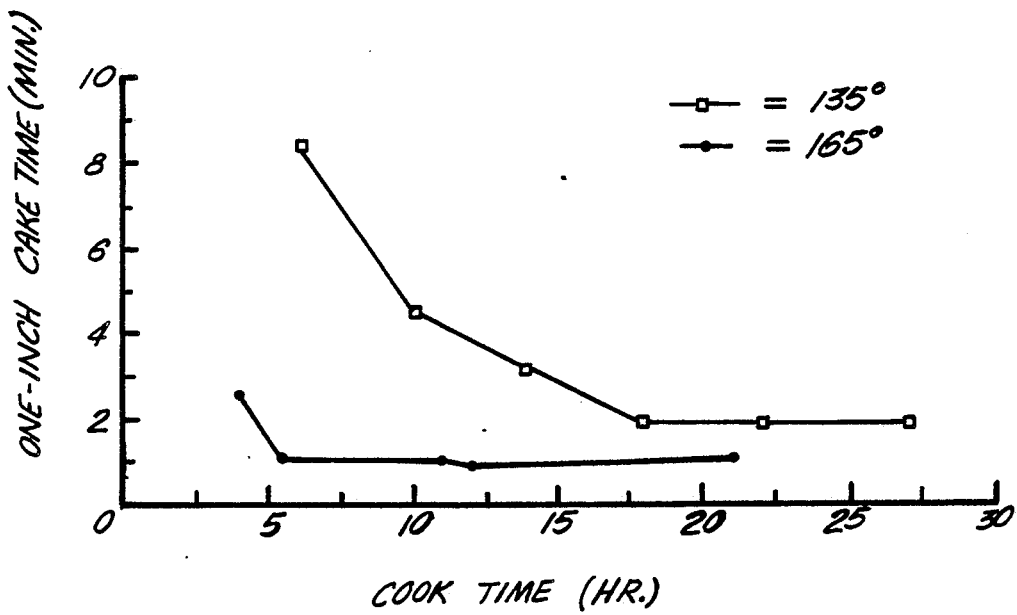
FIG. 1 is a graph of One-Inch Cake Time (minute) vs. Cook Time (hour).

For the purposes of this disclosure, the N,N'-alkylene-bis(tetrabromophthalimide) and the N,N'-bis(tetrabromophthalimide) will hereinafter be referred to collectively as bisimide and are represented by the formula,

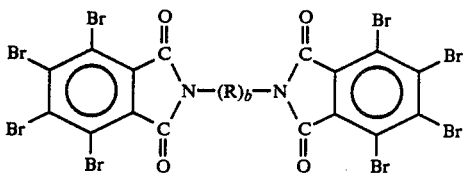

wherein R is an alkylene radical containing 1 to 6 carbon atoms and b is 1 or 0. R can be a branched or be a straight chain radical. R is preferably methylene, (—$CH_2$—), or ethylene, (—$CH_2$—$CH_2$—). When b is 0, the bonding between the two cyclic groups is via a N—N bond.

The bisimide precipitate and product are predominantly comprised of bisimide. Impurities which may be present are solvent, tetrabromophthalic anhydride, tetrabromophthalimide, N,N'-alkylene-bis(propionamide), N,N'-bis(propionamide) and N-(ethylene-2-tetrabromophthalimido)propionamide. Generally, the bisimide will constitute at least 98 wt. % of the bisimide product.

The diamine that is used in the process of this invention can be represented by the formula: $H_2N$—(R-$)_b$—$NH_2$ wherein R and b are as defined above. For example, the diamine can be 1,1-diaminomethane, 1,2-diaminoethane, 1,1-diaminopropane, 1,3-diaminopropane, 1,4-diaminobutane, 1,5-diaminopentane, 1,6-diaminohexane, hydrazine, etc. The diamine reactant can also be a mixture of diamines, however, the final product obtained will not be a single specie but rather will be a mixture of species as determined by the diamine mixture used. Preferred diamines are hydrazine and 1,2-diaminoethane as they yield particularly useful white flame retardant products. The diamine can be added neat or in solution with a solvent, e.g. o-, m-, p-xylene or a mixture thereof. Technical or commercial grade xylene can be used, such xylene being comprised of a mixture predominate in o-, m- and p- xylenes, and to a lesser extent, ethyl benzene.

The partially or totally diamine neutralized mono-, di- or tri- carboxylic acid salts which can be used in the practice of this invention will, hereinafter, simply be referred to as diamine salts. The carboxylic acid constituent of the diamine salt is derived from an acid having a dissociation constant not greater than about $1.0 \times 10^{-3}$ at 25° C. The preferred derivative acids are alkanoic and aralkanoic carboxylic acids containing 2 to 12 carbon atoms and mixtures thereof. Most preferred of these acids are alkanoic acids having a dissociation constant less than $1.8 \times 10^{-5}$ at 25° C. and containing 2 to 6 carbon atoms. Exemplary of suitable derivative carboxylic acids are: acetic acid, propionic acid, isobutyric acid, valeric acid, hexanoic acid, toluic acid, acrylic acid, benzoic acid, bromobenzoic acid, phenylacetic acid, p-methylphenylacetic acid, alpha-phenylpropionic acid, succinic acid, glutaric acid, adipic acid, and mixtures thereof. Propionic acid is preferred. The cationic diamine constituent of the diamine salt can be derived from the $H_2N$—(R)$_b$—$NH_2$ diamines and the mixtures thereof which are discussed above. Preferred salts are the hydrazine and diamonoethane salts. Especially preferred are the hydrazine and diaminoethane salts of propionic acid.

It is also possible to use a mixture of the above-described diamines and diamine salts in the practice of the process of this invention. For simplicity, such mixtures are to be taken as being included in the phrase "diamine or diamine salts" as hereinafter used.

The solvent used in the process of this invention is one in which the tetrabromophthalic anhydride is soluble and in which the the bisimide precipitate is substantially insoluble. Further, the solvent should not adversely affect the yield, the color or the physical characteristics of the bisimide product.

It is preferred that the solvent chosen be one which will be at its boiling point under the reaction temperature and pressure. By having a boiling condition, the reaction temperature can easily be kept fairly constant during the diamine or diamine salt addition and cooking steps. It is particularly useful to reflux the boiled off solvent vapor back to the reaction mass. This refluxing is performed conventionally by means of a condenser and return line. If the solvent chosen does not boil under reaction conditions, provision can be made to maintain the constancy of the reaction temperature, such as by providing the reactor with a heating or cooling jacket.

The solvent can be comprised of a single constituent or a plurality of constituents. A necessary constituent is a mono-, di- or tri- carboxylic acid having a dissociation constant not higher than $1.0 \times 10^{-3}$ at 25° C. Exemplary of suitable carboxylic acids are: acetic acid, propionic acid, isobutyric acid, valeric acid, hexanoic acid, toluic acid, acrylic acid, benzoic acid, bromobenzoic phenylacetic acid, p-methylphenylacetic acid, alpha-phenylpropionic acid, succinic acid, glutaric acid, adipic acid, and mixtures thereof. Preferred carboxylic acids are the alkanoic and the aralkanoic carboxylic acids containing 2 to 12 carbon atoms, with alkanoic acids having a dissociation constant of less than $1.8 \times 10^5$ at 25° C. and containing 2 to 6 carbon atoms being more preferred. A most preferred acid is propionic acid. Quantitatively, the mono-, di- or tri- carboxylic acid is present in the solvent in an amount in excess of about 15 wt %, based upon the total weight of the solvent. Preferred amounts are within the range of from about 25 wt % to about 100 wt %. Most preferred amounts are 30 wt % and 100 wt %.

An optional solvent constituent is an aromatic hydrocarbon or an aromatic halohydrocarbon which has a boiling point above about 80° C. at atmospheric pressure. Examples of suitable aromatic compounds are: benzene; o-, m-, p- xylene, and mixtures of such xylenes; mesitylene; cumene; pseudocumene; o-, m-, p- diethylbenzene, and mixtures of such diethylbenzenes; ethylbenzene; o-, m-, p- dichlorobenzenes, and mixtures of such dichlorobenzenes; chlorobenzene; and mixtures of the foregoing. Preferred are o-, m-, p- xylene and mixtures thereof. Technical or commercial grades of xylene are also preferred, which grades can contain significant quantities of ethylbenzene.

The solvent can contain other constituents which may or may not contribute to the solvent function provided that such constituents do not unduly interfere with the process or with the quality of the bisimide product formed.

One preferred solvent is comprised essentially of propionic acid, say about 99+wt % propionic acid. Other preferred solvents are those which contain from about 85 wt % to about 70 wt % o-, m- or p- xylene or mixtures thereof, and from about 15 wt % to about 30 wt % propionic acid, all based upon the total weight of the solvent.

The tetrabromophthalic anhydride/solvent solution provided to the reaction vessel can be formed in the reaction vessel or can be formed exteriorly of the reaction vessel and then added thereto.

The reaction between the tetrabromophthalic anhydride and the diamine or the diamine salt to produce the bisimide precipitate should occur at a temperature within the range of from about 140° C. to about 200° C. The use of such temperatures is beneficial as the filterability of the bisimide precipitate is enhanced as compared against the case in which lower temperatures are used. Other benefits include the lack of the necessity to remove water during the diamine or diamine salt addition and the realization of shorter reaction times. Temperatures much in excess of 200° C. are undesirable as higher reaction pressures will be needed and there is the possibility that the solvent will react with the bisimide. A preferred temperature is within the range of from about 150° C. to about 170° C. A most preferred range is from about 160° C. to about 170° C.

The reaction pressure chosen will be that pressure which is required to enable the obtainment of the reaction temperature and the presence of the solvent as a liquid in the reaction mass. For many solvents, the pressure, therefore, will be superatmospheric. For higher boiling solvents atmospheric operation may be possible. Since reflux operation is preferred, the preferred pressures will be those which provide such operation. When using the preferred xylene and propionic acid solvent, the preferred pressure is within the range of from about 1 atm to about 7 atm.

Water will be produced during the diamine or diamine salt addition by the loss of water from the cyclization of the intermediate, N,N'-(R)$_b$-bis(tetrabromophthalamidic acid). Water removal is optional in the first embodiment of this invention and is not a feature of the second embodiment of this invention.

Though not necessary for the first embodiment, it has been found that the removal of water during the reaction is beneficial as it allows for reuse of the solvent system in subsequent reaction cycles. Water removal can be effected by boiling the water from the reaction mass, by chemical means or by mechanical means. When the water is removed by boiling, the reaction temperature and pressure are chosen to effect such boiling. If the reaction is under reflux conditions, the solvent and water vapors are condensed and then separated in a phase separator, with the solvent being returned to the reaction mass.

Chemical techniques for removing water from the reaction mass include the addition of a dehydrating agent to the reaction mass. Exemplary dehydrating agents are propionic anhydride, acetic anhydride, phosphorous pentoxide and the like.

Mechanical techniques include the use of molecular sieves and the like.

If water removal is not to be effected, as is the case for the second embodiment of this invention, the reaction system simply is not provided with a method for effecting such removal, e.g. a phase separator, such as a Dean Stark trap. Retention of the water during several reactions will ultimately require that the solvent be treated to remove water when the water buildup begins to significantly effect the solvent's boiling point. The fact that a relatively white bisimide product can be obtained while retaining water in the reaction mass is believed to be due to the use of high temperatures (140° C. to 200° C.) during the diamine or diamine salt addition.

While water retention in the reaction mass is not desired from the standpoint of reusing the solvent system, it has been found that the presence of water in the reaction mass is beneficial as it will inhibit the production of N-(ethylene-2-tetrabromophthalimido) propionamide and N-(tetrabromophthalimido) propionamide.

For all of the foregoing concerning water removal, it is to be understood that water removal means the physical removal of water from the reaction mass, the chemical changing of the water or the inactivating or bonding of the water by mechanical means.

The quantitative relationship between the tetrabromophthalic anhydride and the diamine or diamine salt used should be substantially stoichiometric, i.e. a molar ratio of anhydride to diamine or diamine salt within the range of from about 1.9:1 to about 2.1:1. A preferred ratio is within the range of from about 2:1 (0% molar excess anhydride) to about 2.07:1 (3.5% molar excess anhydride).

The rate of diamine or diamine salt addition is believed to be a significant contributing factor to particle size and product color. Slow diamine or diamine salt addition rates yield a product having a larger particle size and a higher yellowness index value. Thus, to obtain good product color, the diamine is added as quickly as is practical without causing the process temperature to get out of control. (A rise in temperature is to be expected as the reaction of the diamine or diamine salt with the anhydride reactant is highly exothermic.) On the other hand, to obtain larger particle sizes the addition should be over a long period of time. Even though the sphericity of the particles is the largest factor in determining filterability, very small particle size does contribute to lowering filterability qualities. Thus, the practitioner of this invention will have to balance between the product color and filterability in choosing the diamine or diamine salt addition rates. This choice is made based upon emperical study considering the requirements of the final product, filtering equipment available and the process economics desired.

The cooking step featured in the first embodiment of the process of this invention increases the filterability of the bisimide product from the reaction mass. Initially, the bisimide precipitate will generally have a plate-like form which makes it difficult, if not impossible, to filter within a short period of time. After cooking, it has been observed that the sphericity of the particles making up the cooked bisimide product is greater than that of the pre-cooked bisimide precipitate particles. With this enhancement in sphericity, the filtration time can be cut drastically. For example, an increase in sphericity by a factor within the range of from about 1.5 to about 5 can reduce filtration time, as measured by the procedure of Example I, by a factor within the range of from about 0.45 to about 0.04. The lower filtration times are realized with the higher sphericity values.

The cooking temperature can be within the range of from about 140° C. to about 200° C. Temperatures much above 200° C., should be avoided so as to not promote reaction between the solvent and the bisimide precipitate. Thus, preferred cooking temperatures are within the range of from about 150° C. to about 170° C. Most highly preferred cooking temperatures are within the range of from about 160° C. to about 170° C.

The cooking period is that period of time which effects the increase in sphericity sought. It has been found that the higher cooking temperatures, e.g. 160° C. to 170° C. require substantially shorter cooking times than do the lower temperatures, e.g. 140° C. to 150° C. Also, it is possible, with the higher temperatures, to obtain a bisimide product having a lower filtration time than that which is obtainable with the lower temperatures. It has been found that for any given cooking temperature there is a cooking period beyond which further cooking is of little consequence in decreasing filtration times. Thus, the practitioner of this invention would select a desired filtration time for the bisimide precipitate and then determine by trial and error the cooking period needed to obtain that filtration time, it being realized that there is a bottom limit to the filtration time achievably by the process of this invention. Generally, using the procedure of Example I, one-inch cake formation times as low as about 1 minute are obtainable. The cooking period, at 160° C. to 170 C, needed for the lowest filtration times is within the range of 2 hours to about 5 hours.

It is to be understood that the cooking step can be performed on the reaction mass immediately after the diamine or diamine salt addition is finished or can be performed on the bisimide precipitate which has been recovered from the reaction mass after the diamine or diamine salt addition. The former is preferred. When the latter procedure is used, a slurry containing a liquid and the bisimide precipitate must be formed, which slurry is then subjected to the cooking conditions.

After cooking, the bisimide precipitate obtained is recovered, as the bisimide product, from the reaction mass by any conventional means, e.g. filtration, centrifugation, etc. For commercial production, recovery of the product by use of a rotary vacuum filter is believed to be preferred. It has also been found that the recovery rate can be increased, in some cases, by effecting the recovery at a temperature of from about 65° C. to about 85° C.

The cooking step may be used as an added step in the second embodiment of this invention, but is not required even though filtering times may be higher than those realized with cooking step. In any case, the final bisimide product of this embodiment is recovered in the same manner described above for the bisimide product of the first embodiment.

It is believed that, in both embodiments, the sphericity of the bisimide precipitate is enhanced somewhat during the diamine or diamine salt addition step as the reaction temperature during this step is similar to the cooking step temperature. The first formed bisimide product will be most affected as it will have a longer exposure to the reaction temperature than is the case for the last formed bisimide product.

After recovery, the bisimide product, whether exposed to the cooking step or not, is preferably washed to reduce the content of any non-bisimide impurities which are present. Washing can be effected by using any wash solvent which is capable of solubilizing to some degree the impurities sought to be removed. A useful solvent is an alkanol, such as methanol. However, it is most preferred to wash the bisimide product with a wash solvent mixture containing a nonpolar constituent, such as an aromatic hydrocarbon or halohydrocarbon, and an organic acid. The nonpolar and organic acid constituents of the wash solvent can be, respectively, any of the aromatic hydrocarbons or halohydrocarbons and any of the organic acids before described for the constituents of the solvent used in the process of this invention. It is most preferred to use the same wash solvent constituents which were used to prepare the bisimide product since such eliminates the need for separation between the reaction filtrate and the wash filtrate. A preferred wash solvent is one comprised of xylene and propionic acid in the same proportions as that used for the xylene and propionic reaction solvent before described. Use of the preferred wash solvent yields a bisimide product having a very low acid number. This is a surprising result in view of the presence in the solvent of the organic acid constituent.

When washing the bisimide product, at least one void volume of the wash solvent should be used. Since the porosity of the bisimide product is typically 0.75 to 0.8, the wash volume should be 0.75 to 0.8 cake volumes. A void volume is defined as that volume of bisimide product to be washed which is not occupied by bisimide product particles. The wash temperature can vary from 0° C. to 150° C. depending upon the vapor pressure of the solvents and the equipment limitations. In general, the higher the temperature of the wash, the shorter the wash time. For most solvent systems, the optimum wash temperature is up to about 80° C., which is the upper temperature limit for polypropylene filter media which can be used in recovery of the bisimide product after washing. Further washing with water or an alcohol is not necessary and, from a process economy viewpoint, not desirable.

After washing, the washed bisimide product is dried conventionally, say for a period of from about 12 to about 48 hours at a temperature of from about 125° C. to about 140° C.

The bisimide product produced by the process of this invention not only has good thermal stability and resistance to UV degradation, but also has a low acid number, less than about 1.0, and a high bromine content, i.e. within the range of from about 60% to about 67%. Washing with the preferred wash solvent can give a bisimide product having an acid number as low as 0.05. Hunter Colorometer values for the bisimide product produced with water removal are exemplified by $L=90.30$, $a=-1.31$, $b=5.58$, and a yellowness index $(Y.I.)=10.31$, with the product having a particle size distribution of 90%<8 microns, 50%<4 microns and 10%<1.5 microns.

The bisimide product of this invention may be used as a flame retardant in formulation with virtually any flammable material. The material may be macromolecular, for example, a cellulosic material or a polymer. Illustrative polymers are: olefin polymers, cross-linked, and otherwise, for example, homopolymers of ethylene, propylene, and butylene; copolymers of two or more of such alkylene monomers, and copolymers of one or more of such alkylene monomers, and any other copolymerizable monomers, for example, ethylene/propylene copolymers, ethylene/ethyl acrylate copolymers, and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyd resins; phenolics; elastomers, for example, butadiene/styrene copolymers and butadiene/acrylonitrile copolymers; terpolymers of acrylonitrile, butadiene, and styrene; natural rubber; butyl rubber; and polysiloxanes. The polymer may also be a blend of various polymers. Further, the polymer may be, where appropriate, cross-linked by chemical means or by irradiation.

The amount of bisimide product used in a formulation will be that quantity needed to obtain the flame retardancy sought. It will be apparent to those skilled in the art that for all cases no single precise value for the proportion of the bisimide product in the formulation can be given, since this proportion will vary with the particular flammable material, the presence of other additives, and the degree of flame retardancy sought for in any given application. Further, the proportion necessary to achieve a given flame retardancy in a particular formulation will depend upon the shape of the article into which the formulation is to be made, for example, electrical insulation, tubing, and film will each behave differently. In general, however, the formulation may contain from about 3 to about 40 wt %, preferably 10 to 30 wt %, of the bisimide product when it is the only flame retardant compound in the formulation. The wt % amounts are based upon the total weight of the formulation.

It is especially advantageous to use the bisimide product of this invention and an inorganic compound, especially the oxide, of a Group V element, for example, bismuth, arsenic, phosphorus, and especially antimony, in the formulation. Of these compounds, antimony oxide is especially preferred. If such a compound is present in the formulation, the quantity of bisimide product needed to achieve a given flame-retardancy is accordingly reduced.

Formulations containing a bisimide product/inorganic compound flame retardant system may contain up to about 40% by weight of the system, preferably between 10 and 30% by weight.

It is believed that the bisimide product and the inorganic compound will react under the conditions of combustion of a flammable material to form inorganic bromine compounds, e.g., hydrogen bromide and oxybromides, which assist in retarding combustion. The bromine-bearing bisimide product also acts as a flame retardant independently, and the proportions of the bisimide product and inorganic compound in a flame retardant system are a matter of choice, depending on the material in which the system is to be incorporated and commercial considerations. Generally, the bisimide product and the inorganic compound are in a weight ratio of from about 1:1 to about 7:1, and preferably of from about 2:1 to about 4:1.

The formulations containing the bisimide product of this invention may contain any of the additives usually present in such formulations, e.g. glass fibers, plasticizers, nucleating agents, antioxidants, filler, pigment, UV stabilizers, etc.

The inventions disclosed herein are illustrated by the following Examples.

EXAMPLE I

The one-inch cake times (minutes) used to make the plot in FIG. 1 were obtained by the following procedure.

A reaction slurry prepared by the method of Example III was heated to 80° C. with light agitation. The slurry was then poured into a medium-frit, 95-mm internal-diameter Buchner funnel. As soon as vacuum was applied (28 in Hg), a solid cake was observed to form on top of the frit. A stop watch was used to determine the length of time required for a one-inch-thick cake to form following the application of vacuum. The time value obtained is referred to as the "one-inch cake time".

EXAMPLE II

Figure 2:
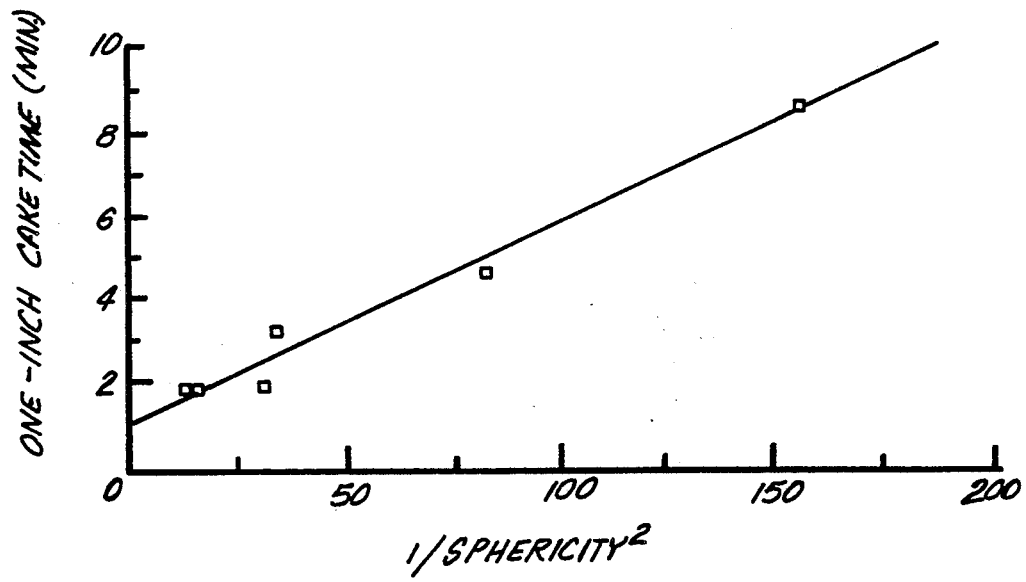
FIG. 2 is a graph of One-Inch Cake Time (minute) vs. 1/Sphericity$^2$.

Average sphericity values used in making the plot in FIG. 2 were obtained in accordance with the following method.

The surface area, $S_p$, per gram of dried bisimide product was measured with standard Brunauer, Emmett and Teller (BET) apparatus. The volume, $V_p$, per gram of dried bisimide product was determined in a helium-displacement stereo pycnometer made by Quanta Chrome Corporation. The volume-average particle diameter, $D_p$, of the dried bisimide product was determined using a laser-light-scattering sizer, i.e. a Microtrac ® made by Leeds and Northrup, Microtrac Division. From these measurements the sphericity was then calculated by $$\text{Sphericity} = \frac{6}{D_p}\left[\frac{V_p}{S_p}\right]$$

Thus, for the rightmost point of FIG. 2, $S_p$ was 7.97 $m^2/g$, $V_p$ was $3.55 \times 10^{31}$ $^7 m^3/g$, and $D_p$ was $3.53 \times 10^{-6}$m. The average sphericity was found to be 0.08. The abscissa on FIG. 2 (1/sphericity$^2$) was then 156.

EXAMPLE III

To a reaction vessel equipped with a condenser, stirrer, a Dean-Stark trap, and a temperature controllable heating mantel was charged 405.0 g of mixed xylenes, 180.0 g of propionic acid, and 156.5 g of tetrabromophthalic anhydride. The mixture was heated to a temperature of 165° C. A solution containing 9.9 g of diaminoethane and 15 g of mixed xylenes was then added to the reactor over a period of about 60 minutes. An aqueous phase containing water and propionic acid was separated from the reflux stream with the Dean-Stark trap. The organic phase containing the xylenes and propionic acid was returned to the reactor. After the diaminoethane addition was completed the reaction mass was cooked at a temperature of 165° C. for about 5 hours. The cooked reaction mass was then cooled to 80° C. and filtered. The recovered precipitate was washed with a wash solvent comprising 70 wt % commercial grade xylene and 30 wt % propionic acid. The washed precipitate was then dried at 125° C. in a forced air oven for 16 hours. The dried product contained about 98% N,N'-ethylene-bis(tetrabromophthalimide). The overall yield was 94 wt. %.

EXAMPLE IV

The procedure of Examples I and II were used to measure the sphericity and the filtration time of various bisimide products produced by the process described in Example III, which process was modified to have the different cooking temperatures and times which are shown in the graph of FIG. 1.

In FIG. 1 it is seen that the higher cooking temperature (165° C.) took a significantly shorter time to obtain a low filtration time than did the lower cooking temperature (135° C.). Also, the higher cooking temperature obtained the lowest filtration times. Another aspect shown in FIG. 1 is that the extension of cooking time, in both cases, beyond a certain point has little or no effect in reducing filtration time.

In FIG. 2 the effect of sphericity on filtration times is shown. The data used came from bisimide products used to obtain the data points for the 135° C. plot in FIG. 1. It is seen that the closer the value of sphericity approaches 1, the shorter the filtration time obtained. When the sphericity value is 1, the particles measured are perfect spheres.

EXAMPLE V

To a glass-lined reactor which was jacketed for heating and cooling, and which was equipped with an agitator and a glass-lined overhead reflux system, was charged 796 pounds of tetrabromophthalic anhydride. Also charged was 900 pounds of propionic acid and 2,174 pounds of commercial grade xylene. Commercial grade xylene contains a mixture of o-, m- and p-xylenes and about 18 wt % ethylbenzene. The reactor jacket was used to heat the reactor to reflux (158° C.) for 1 hour to remove water from the reactor contents. Following this refluxing period a solution containing 50.2 pounds of diaminoethane and 14.5 pounds if commercial grade xylene was fed to the reactor over a period of about 2.75 hours. During this feed period the reactor was maintained at a temperature of 163° C. and a pressure of 20 psig. After the feed period was completed the reactor was maintained at about 165° C. for an additional 5 hours. This 5 hour period represented a cook time. During both the feed and cook periods the reaction mass was at reflux, with an aqueous component being removed from the reflux stream. The aqueous component comprised water and propionic acid. This removed aqueous component was recovered and was found to weigh 61 pounds. The reactor contents were cooled to 80° C. by cooling the reactor with the reactor jacket for about 1.25 hours. The reactor contents were fed to a 48 inch by 30 inch perforated basket, centrifuged, and the solids were separated from the remainder of the reactor contents. The product was wet and in cake form. This product was washed with a mixture of propionic acid and commercial grade xylene. The wash temperature was 80° C. The propionic acid and commercial grade xylene wash solvent used weighed 3,164 pounds and contained 955 pounds of propionic acid and 2,209 pounds of commercial grade xylene. After washing, a total of 870 pounds of wet product, which contained 10.4 wt. % wash solvent, was recovered. This represents a yield of 95.5% based upon the amount of tetrabromophthalic anhydride originally charged to the reactor.

The wet product was then dried in a rotating vacuum drier along with product from other reactions. The drier was operated at a pressure of 10 mm Hg absolute in a temperature of 135° C. The rotating vacuum drier was operated for about 24 hours. Dried product had a loss on drying (LOD) analysis of less than 0.2%.

The product gave the characteristics shown in Table I.

TABLE I

| | |
|---|---|
| Initial Melting Point, °C. (DSC) | 452.0 |
| Loss on Drying, 180° C., Full Vacuum, 1 hour | .05 |
| Acid-Number, mg KOH/g | .05 |
| Iron content, ppm | 11.0 |
| Particle size, microns | |
| 10% less than | 1.5 |
| 50% less than | 4.0 |

TABLE I-continued

| | |
|---|---|
| 90% less than | 8.0 |
| Hunter Colormeter Values | |
| L | 89.5 |
| a | −2.0 |
| b | 6.0 |
| YI (ASTM 1313) | 10.8 |

EXAMPLE VI

A polybutyleneteraphthalate-based formulation containing polybutyleneteraphthalate, 30 wt % glass, 5 wt % antimony trioxide, and 11 wt % of the dried product from Example V was prepared by conventional techniques utilizing a twin-screw extruder at 250° C. to 260° C. The extruded formulation was used in forming test bars. The test bars were formed by injection molding at a temperature of about 260°-266° C. The test bars had good U.V. stability as is seen in Table II.

TABLE II

| U. V. Stability (48 Hours) | |
|---|---|
| Initial Values | |
| L | 84.1 |
| a | −1.3 |
| b | 7.0 |
| YI (ASTM 1313) | 12.4 |
| Final Values | |
| L | 84.8 |
| a | −1.4 |
| b | 9.7 |
| YI (ASTM 1313) | 17.0 |
| $\Delta E_{48}$ 2.75 | |

The following table illustrates various physical properties of the test bars prepared from the product produced by the process described in Example III.

TABLE III

| Test | Result |
|---|---|
| Tensile Yield, psi | 12306 |
| Tensile Elastic Mod., psi × $10^5$ | 7.5 |
| Elongation % | 2.5 |
| Flexural Strength, psi | 20742 |
| Flexural Elastic Mod., psi × $10^5$ | 11.2 |
| IZOD Impact - ⅛", ft. lb/in. Notch | 1.24 |
| HDT - °C. (⅛"), 264 psi | 209 |
| Melt Index g/10 min | 35.13 |
| Dielectric Const. $10^6$ Hz | 3.31 |
| Dielectric Breakdown Strength, KV/Mil. | .391 |
| Volume Resistivity × $10^{16}$ ohm cm | 1.1 |
| Surface Resistivity × $10^{16}$ ohms | 1.1 |
| Dissipation Factor | .0078 |
| ⅛" | V-O |
| UL-94 1/16" | V-O |
| 1/32" | V-O |
| L.O.I. | 34.6 |

EXAMPLE VII

Undried and unwashed cake produced in accordance with Example V was collected. One cake portion was washed with methanol and another was washed with a solvent comprised of 70 wt. % commercial grade xylene and 30 wt. % propionic acid. 2.9 void volumes of wash were used in each case. Following the washes, the cake was dried and the acid number (mg of KOH per gram of product required for neutralization) and color change ($\Delta E_{48}$ from a Hunter Colorimeter following exposure to UV radiation for 48 hours) in polybutyleneterephthalate plaques were determined. The results were as follows:

|  | Wash Solvent | |
| --- | --- | --- |
|  | Methanol | Xylene + Propionic Acid |
| Acid No. | 0.34 | 0.21 |
| $\Delta E_{48}$ | 4.09 | 3.52 |

The xylene and propionic acid wash solvent produced a product with lower acid number and less color change than that produced with a methanol wash.

what is claimed:

1. A process for preparing a bisimide product which principally contains a bisimide of the formula,

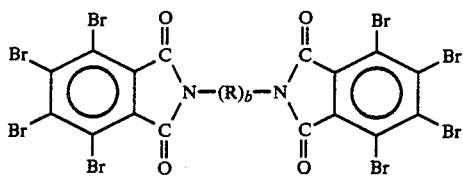

wherein R is an alkylene radical containing 1 to 6 carbon atoms and b is 1 or 0, said process comprising:
  (a) providing, in a reaction vessel, a solution containing tetrabromophthalic anhydride and a solvent, which solvent contains at least about 15 wt % of a mono-, di- or tri- carboxylic acid having a dissociation constant not higher than $1.0 \times 10^{-3}$ at 25° C.;
  (b) forming, at a temperature within the range of from 140° C. to about 200° C., a reaction mass by adding to said solution, a diamine of the formula,

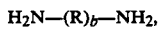

a diamine salt formed by the partial or total diamine neutralization of a mono-, di- or tri- carboxylic acid having a dissociation constant not higher than $1.0 \times 10^{-3}$ at 25° C., or a mixture of said diamine and said diamine salt, said formation of said reaction mass resulting in the production of a bisimide precipitate and water which become components of the reaction mass;
  (c) retaining in the reaction mass, during its formation, at least a substantial portion of the water produced during such formation;
  (d) terminating said addition of the diamine, diamine salt or mixture when the molar ratio of said tetrabromophthalic anhydride initially present in the solution to said diamine and/or diamine salt added is within the range of from about 1:9:1 to 2.1:1;
  (e) after the termination of said addition, cooking said reaction mass for a period of time at a temperature within the range of from about 140° C. to about 200° C. so as to obtain an increase in the average sphericity of the particles comprising said bisimide precipitate, said sphericity being defined as the ratio of the surface area of a sphere having a volume of the particle being measured to the surface area of that particle, said reaction mass comprising water, said mono-, di or tri-carboxylic acid and said bisimide precipitate during said cooking period; and
  (f) recovering, as said bisimide product, the cooked bisimide precipitate from the remainder of said reaction mass, which remainder comprises water and said mono-, di-, or tri-carboxylic acid.

2. The process of claim 1 wherein said solvent comprises propionic acid.

3. The process of claim 1 wherein said solvent comprises propionic acid and o-, m-, p- xylene or mixtures of such xylenes.

4. The process of claim 3 wherein said propionic acid is present in an amount within the range of from about 15 to about 30 wt %.

5. The process of claim 1 wherein said solvent is predominantly propionic acid.

6. The process of claim 1 wherein R is an ethylene radical and b is 1.

7. The process of claim 1 wherein said reaction mass, during said addition, is at a temperature within the range of from about 150° C. to about 170° C.

8. The process of claim 7 wherein said cooking occurs at a temperature within the range of from about 160° C. to about 170° C.

9. The process of claim 8 wherein said cooking occurs over a period within the range of from about 2 hours to about 5 hours.

10. The process of claim 1 wherein said recovered bisimide product is washed with an alkanol.

11. The process of claim 1 wherein said recovered bisimide product is washed with a wash solvent comprised of a non-polar solvent and an organic acid.

12. The process of claim 11 wherein said non-polar solvent is an aromatic hydrocarbon or an aromatic halohydrocarbon.

13. The process of claim 11 wherein said organic acid in said wash solvent is a mono-, di- or tri- carboxylic acid having a disassociation constant not higher than $1.0 \times 10^{-3}$ at 25° C.

14. The process of claim 12 wherein said organic acid in said wash solvent is a mono-, di- or tri- carboxylic acid having a disassociation constant not higher than $1.0 \times 10^{31}{}^3$ at 25° C.

15. The process of claim 11 wherein the volume of said wash solvent used is at least one void volume.

16. The process of claim 14 wherein the volume of said wash solvent used is at least one void volume.

17. The process of claim 16 wherein said washing occurs at a temperature within the range of from about 0° C. to about 200° C.

18. The process of claim 4 wherein R is an ethylene radical and b is 1.

19. The process of claim 18 wherein said cooking occurs at a temperature within the range of from about 160° C. to about 170° C. for a period of time within the range of from about 2 hours to about 5 hours.

20. The process of claim 19 wherein said recovered bisimide product is washed with a wash solvent comprised of from about 15 to about 30 wt % propionic acid and from about 85 to about 70 wt % o-, m- or p- xylene, mixtures of such xylenes or mixtures of ethylbenzene and o-, m- and p-xylenes, and the amount of said wash solvent used to wash is at least one void volume.

* * * * *

UNITED STATES PATENT AND TRADEMARK OFFICE
CERTIFICATE OF CORRECTION

PATENT NO. : 4,990,626

DATED : FEBRUARY 5, 1991

INVENTOR(S) : DONALD O. HUTCHINSON ET AL.

It is certified that error appears in the above-identified patent and that said Letters Patent is hereby corrected as shown below:

Column 13, line 53, reads "of from about 1:9:1 to 2.1:1" and should read -- of from about 1.9:1 to 2.1:1 -- .

Column 14, line 43, reads "$1.0 \times 10^{31\ 3}$ at $25^{\circ}C$." and should read -- $1.0 \times 10^{-3}$ at $25^{\circ}C$ .-- .

Signed and Sealed this

Seventh Day of July, 1992

Attest:

DOUGLAS B. COMER

*Attesting Officer*   Acting Commissioner of Patents and Trademarks